(12) United States Patent
Hasui et al.

(10) Patent No.: US 10,342,968 B2
(45) Date of Patent: Jul. 9, 2019

(54) ELECTRODE PAD USED FOR IONTOPHORESIS TREATMENT

(75) Inventors: Akihiro Hasui, Kagawa (JP); Atsuhiko Shiraishi, Kagawa (JP); Ken-ichi Hattori, Kagawa (JP); Shinji Tanaka, Kagawa (JP); Hirokazu Takahashi, Kagawa (JP); Makoto Takahashi, Hokkaido (JP)

(73) Assignee: TEIKOKU SEIYAKU CO., LTD., Kagawa (JP)

( * ) Notice: Subject to any disclaimer, the term of this patent is extended or adjusted under 35 U.S.C. 154(b) by 0 days.

(21) Appl. No.: 13/995,720

(22) PCT Filed: Dec. 21, 2011

(86) PCT No.: PCT/JP2011/079670
§ 371 (c)(1),
(2), (4) Date: Aug. 2, 2013

(87) PCT Pub. No.: WO2012/086700
PCT Pub. Date: Jun. 28, 2012

(65) Prior Publication Data
US 2013/0310733 A1    Nov. 21, 2013

(30) Foreign Application Priority Data

Dec. 22, 2010    (JP) .................... 2010-285848

(51) Int. Cl.
*A61N 1/04* (2006.01)
*A61N 1/32* (2006.01)
(Continued)

(52) U.S. Cl.
CPC ......... *A61N 1/0448* (2013.01); *A61N 1/0428* (2013.01); *A61N 1/30* (2013.01); *A61N 1/325* (2013.01); *A61M 2037/0007* (2013.01)

(58) Field of Classification Search
CPC ........ A61M 2037/0007; A61M 35/003; A61N 1/30; A61N 1/18; A61N 1/20;
(Continued)

(56) References Cited

U.S. PATENT DOCUMENTS 4,141,359 A    2/1979 Jacobsen et al.
4,693,711 A *  9/1987 Bremer ............... A61B 5/0408
                                                    604/306
(Continued)

FOREIGN PATENT DOCUMENTS

CN    201631907         11/2010
EP    1008365 A1 *  6/2000 ............. A61N 1/044
(Continued)

OTHER PUBLICATIONS

International Search Report dated Jan. 24, 2012 in International (PCT) Application No. PCT/JP2011/079670.
(Continued)

*Primary Examiner* — Bhisma Mehta
*Assistant Examiner* — William R Frehe
(74) *Attorney, Agent, or Firm* — Wenderoth, Lind & Ponack, L.L.P.

(57) ABSTRACT

The present invention verifies a method of reducing skin irritation (particularly, cumulative skin irritation) caused by transdermal administration of a local anesthetic using iontophoresis, and provides an electrode pad for relief from a puncture pain which is safe not only at single administration but also at repeated administrations. The electrode pad comprises a base sheet; an electrode placed on the base sheet; an adhesive sheet placed on the base sheet and having an opening, within which the electrode being exposed; and a medicament reservoir containing a local anesthetic and placed in the opening of the adhesive sheet while being in contact with the electrode. An inner peripheral surface of the
(Continued)

opening of the adhesive sheet and an outer peripheral surface of the medicament reservoir are prevented from coming into contact with human skin while contacting with each other, and thereby skin irritation is reduced.

6 Claims, 14 Drawing Sheets

(51) Int. Cl.
*A61N 1/30* (2006.01)
*A61M 37/00* (2006.01)

(58) Field of Classification Search
CPC . A61N 1/205; A61N 1/22; A61N 1/24; A61N 1/26; A61N 1/28; A61N 1/303; A61N 1/32; A61N 1/325
USPC .......................................................... 604/20
See application file for complete search history.

(56) References Cited

U.S. PATENT DOCUMENTS

| | | | |
|---|---|---|---|
| 4,708,716 A | | 11/1987 | Sibalis |
| 5,032,110 A | * | 7/1991 | Watanabe ................ 604/20 |
| 5,169,382 A | | 12/1992 | Theeuwes et al. |
| 5,246,418 A | | 9/1993 | Haynes et al. |
| 5,928,185 A | * | 7/1999 | Muller ............... A61N 1/0436 604/20 |
| 5,990,179 A | * | 11/1999 | Gyory ................ A61K 9/0009 514/329 |
| 6,006,130 A | * | 12/1999 | Higo .................. A61N 1/0436 604/20 |
| 6,328,728 B1 | * | 12/2001 | Holladay ............ A61K 9/0009 604/501 |
| 6,336,049 B1 | | 1/2002 | Kinbara et al. |
| 2002/0062102 A1 | * | 5/2002 | Keusch ............... A61N 1/0448 604/20 |
| 2003/0060797 A1 | | 3/2003 | Fischer |
| 2005/0228336 A1 | | 10/2005 | Keusch et al. |
| 2006/0089590 A1 | * | 4/2006 | Higuchi ............... A61K 9/0009 604/20 |
| 2007/0197955 A1 | | 8/2007 | Akiyama et al. |
| 2010/0030128 A1 | | 2/2010 | Mitsuguchi et al. |

FOREIGN PATENT DOCUMENTS

| | | | | |
|---|---|---|---|---|
| EP | 1008365 A1 | * | 6/2000 | ............. A61N 1/044 |
| EP | 1944058 A1 | * | 7/2008 | |
| JP | 59-118167 | | 7/1984 | |
| JP | 5-245214 | | 9/1993 | |
| JP | 9-504191 | | 4/1997 | |
| JP | 9-511167 | | 11/1997 | |
| JP | 2000-24121 | | 1/2000 | |
| WO | 95/06497 | | 3/1995 | |
| WO | 95/26782 | | 10/1995 | |
| WO | 2007/029611 | | 3/2007 | |
| WO | 2007/043605 | | 4/2007 | |

OTHER PUBLICATIONS

FDA Home Page: http://www.accessdata.fda.gov/drugsatfda_docs/nda/2004/021504s000_Lidosite_PharmR.pdf (pp. 35-37).
International Preliminary Report on Patentability and Written Opinion of the International Searching Authority dated Jul. 11, 2013 in International (PCT) Application No. PCT/JP2011/079670.
Supplementary European Search Report dated May 2, 2014 in corresponding European patent Application No. EP 11 85 0105.
English translation of Chinese Office Action dated Mar. 31, 2015 in corresponding Chinese Patent Application No. 201180061853.0.
Office Action dated Jun. 7, 2016 in Japanese Application No. 2015-144181, with English translation.

* cited by examiner

《Comparative Example》

FIG.5
《Referential Example 1》
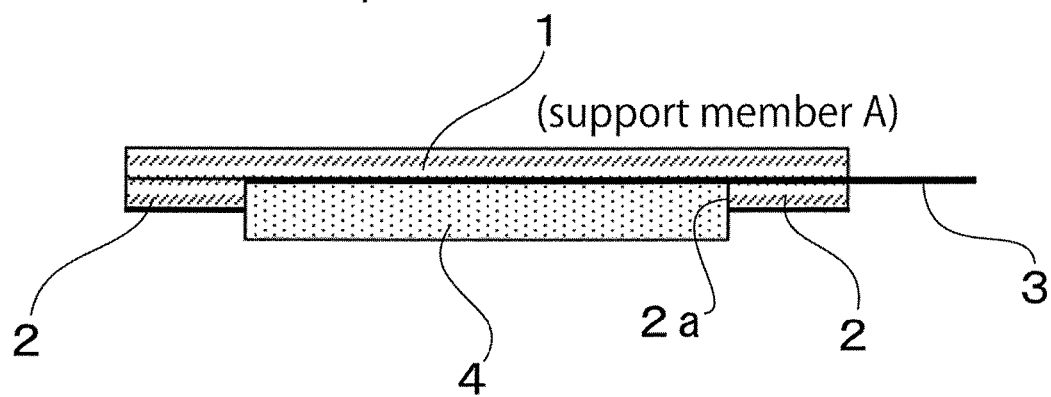
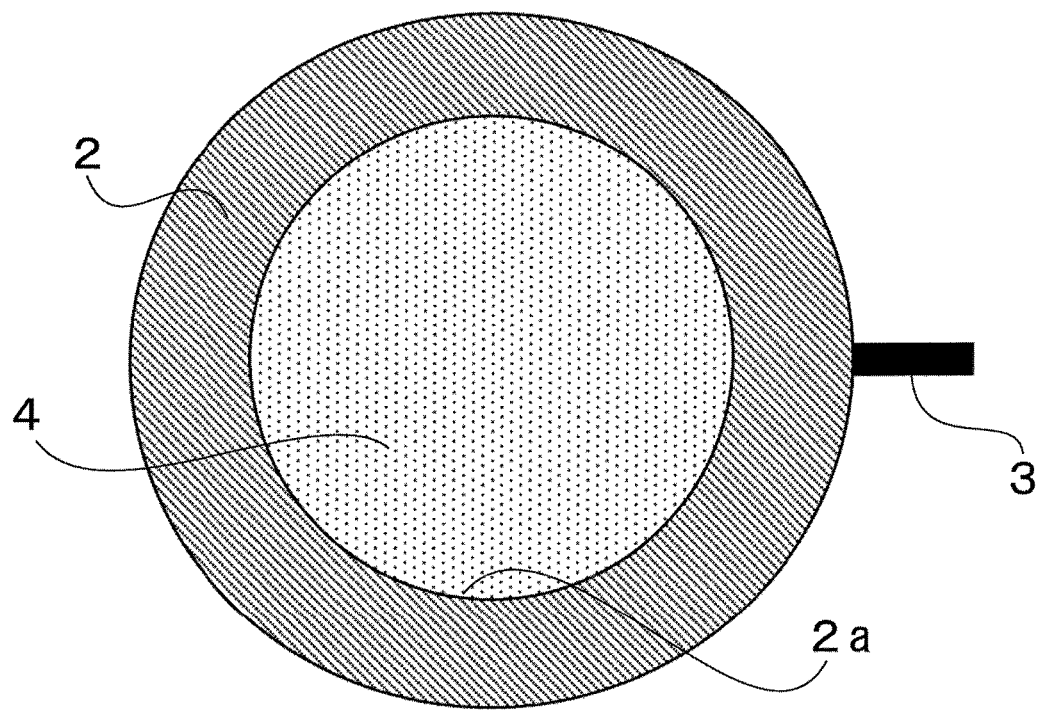

FIG. 6
《Referential Example 2》
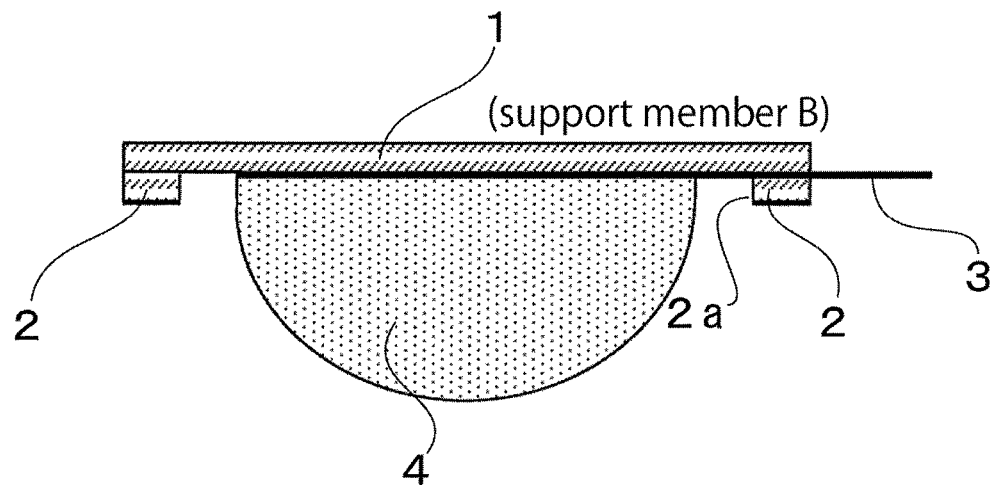
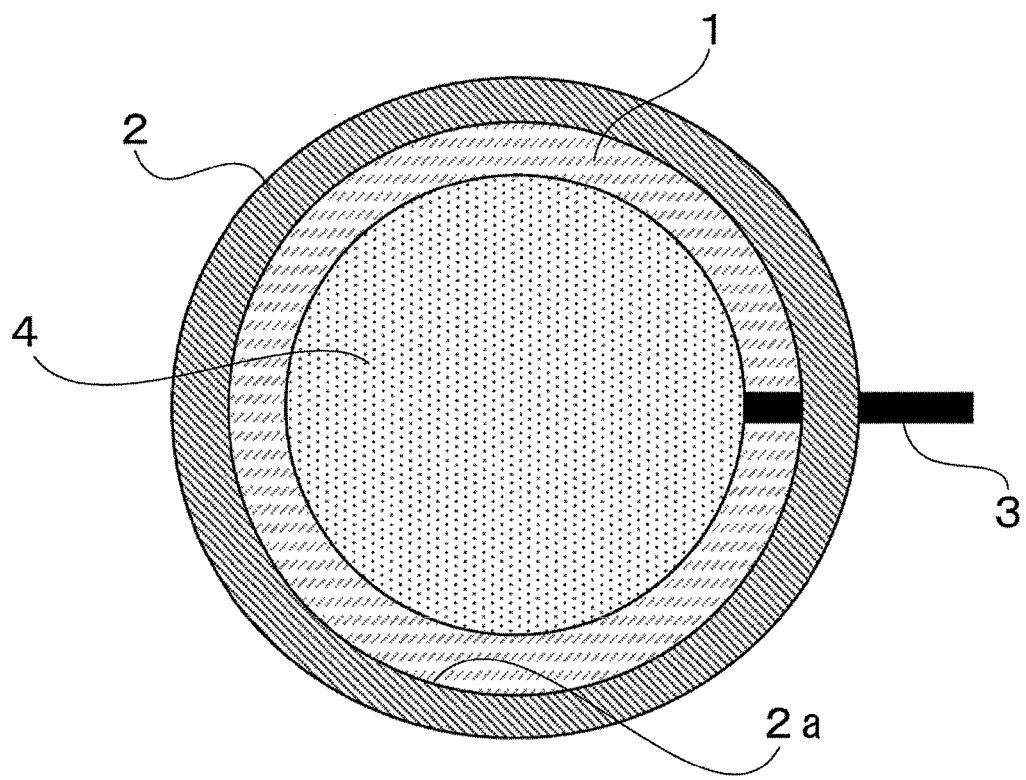

Photograph 1 (skin after repeated administration in Example 1)

Photograph 2 (skin after repeated administration in Example 2)

Photograph 3 (skin after repeated administration in Comparative Example)

Photograph 4 (skin after repeated administration in Example 2)

Photograph 5 (skin after repeated administration in Example 3)

Photograph 6 (skin after repeated administration in Comparative Example)

Photograph 7 (skin after repeated administration in Referential Example 2)

ELECTRODE PAD USED FOR IONTOPHORESIS TREATMENT

TECHNICAL FIELD

The present invention relates to an iontophoresis pad used for transdermal administration of a local anesthetic for alleviating puncture pain. More specifically, the present invention pertains to an electrode pad for reducing irritation caused by repeated treatments.

BACKGROUND ART

In medical front, injections such as intradermal, subcutaneous, intramuscular, and intravenous injections have been conducted frequently. It is not uncommon that needles are kept continuously in human body for instillation, blood donation, and hemodialysis, as well as medicament administration and blood collection for blood test.

Puncture in such injections causes a psychological or physical pain to the patients. Thus, alleviation of this pain during puncture, if possible, may improve the QOL (quality of life) of the patients and facilitate medical treatment.

In Japan, lidocaine patches (which is to be attached for 30 minutes before puncture) have been put on the market, intended for relieving a puncture pain. But, in these lidocaine patches, the onset of action is slow, and it takes long time before puncture.

In medical front, doctor's judgments make a decision, as to whether or not the administration of medicament, the blood collection, or the like should be done. After this judgment, the administration of medicament or the blood collection by an injector is conducted mostly within 30 minutes. There is therefore a demand for a method of transdermally and rapidly administering a local anesthetic within such a limited time, for alleviating the puncture pain.

Iontophoresis is a method of accelerating transdermal absorption of a medicament with use of electric energy, and is capable of intradermally absorbing a large amount of a local anesthetic such as lidocaine in a short time. Thus, it is expected to exhibit a local anesthetic effect in a shorter time than in case where administration of a local anesthetic is done by conventional transdermal absorption, so that puncture and medical treatment can be started without waiting for long time before a pain-removing treatment prior to that puncture is completed (Patent Document 1).

Many studies have been made so far on the skin safety regarding the iontophoresis formulations (electrode pads). In particular, there included studies on the relationship between the skin irritation and electric voltage or current, or reports on a method of reducing skin irritation under the concentration gap of chlorine ions or potassium ions in the skin.

More specifically, regarding an electric transfer type active-agent administering devices, there are reported a method of simultaneously administering a medicament and an anti-inflammatory agent to reduce the skin irritation (Patent Document 2). Further it is reported, in order to reduce the skin irritation, to limit the pH of a reservoir which is to be brought into contact with human skin, and thereby to prevent an increase of the outflow of potassium from the skin (Patent Document 3). In addition, a method of controlling electric voltage and current to reduce the skin irritation is also tried (Patent Document 4).

There is also an attempt to reduce the skin irritation by equalizing the current density in a conductive layer. In Patent Document 5, the current density is regulated by using an electrode which is divided into two or more portions, and each of the portions is equipped with an electric resistor to limit the electric current. But, this device is complex and expensive because the electrode is divided into some portions, and each of which is equipped with the electric resistor.

Besides, in the medical front, sometimes puncture is conducted only once, for example, in single administration of a medicament or blood collection. But sometimes, for example in the blood dialysis, puncture may be conducted three times or more a week, at a predetermined position on an arm. In such a case, there is no information about the skin irritation due to frequent administrations of an iontophoresis formulation for local anesthetic, except the report (Non-patent Document 1) on animals test concerned to the iontophoresis formulation, which was put on the market in the USA.

In particular, a local anesthetic has cytotoxicity and when the skin is repeatedly exposed to a large amount of it, the skin tissue tends to be damaged (skin irritation). In particular, since the iontophoresis can be intradermally absorbed a large amount of a local anesthetic, the damage to the skin by repeated administrations is quite severe. Therefore, there have been a demand for the development of an iontophoresis electrode formulation (electrode pad), which is with less skin irritation and higher safety.

PRIOR ART DOCUMENTS

Patent Documents

Patent Document 1: U.S. Pat. No. 4,141,359
Patent Document 2: Japanese Patent Publication No. H09-511167
Patent Document 3: Japanese Patent Publication No. H09-504191
Patent Document 4: Japanese Patent Publication No. H05-245214
Patent Document 5: Japanese Patent Publication No. 2000-24121

Non-Patent Document

Non-patent Document 1: FDA Home Page: http://www.accessdata.fda.gov/drugsatfda_docs/nda/2004/021504s000_Lidosite_PharmR.pdf (p 35-37)

SUMMARY OF THE INVENTION

Problems to be Solved by the Invention

As described above, there have been very little studies so far, regarding the cumulative skin irritation due to the repeated transdermal administration of a local anesthetic by iontophoresis. Thus, no iontophoresis electrode pad having high safety even in repeated administrations has been developed. The present invention has been made in consideration of this problem. The present invention verifies a method of reducing the skin irritation (particularly, cumulative skin irritation) when a local anesthetic is transdermally administered by iontophoresis, and an object of the invention is to provide a safer electrode pad regarding the alleviating of the puncture pain, not only in single administration but also in repeated administrations.

Means for Solving the Problems

When a local anesthetic is administered (particularly, repeatedly administration) by the iontophoresis, sometimes burn-like stimulation appears, which is presumed to occur because of electric and/or local anesthetic cytotoxicity (for example, Photograph 3 in FIG. 9). First, the inventors have studied the cause of this skin irritation, and concluded that it occurred mainly because of the following two causes.

<Skin Irritation 1 Due to "Boundary Surface">

When a medicament reservoir and a member therearound of an iontophoresis electrode pad, while being brought in contact with each other, come into contact with human skin, a contact surface is formed therebetween through which electric current passes easily. At the contact surface (which will hereinafter be called "boundary surface") between the medicament reservoir in the form of an aqueous gel and the member therearound, a water soluble layer is easily formed, because of which electric current flows easily and current density tends to increase. When the human skin comes into contact with the "boundary surface" during the iontophoresis treatment, large electric current flows and the concentration of a medicament absorbing into the skin becomes high. This is a cause of skin damage.

<Skin Irritation 2 Due to "Adhesion Site">

When a medicament is administered by the iontophoresis, regarding a healthy skin, electric current uniformly flows. But for a damaged skin, it has a site with a reduced electric resistance, where the epidermis or dermis is exposed, and infiltrate or blood may be included there. The electric current flow concentrates on this site of the reduced lower electric resistance, and an amount of the medicament introduced therethrough increases accordingly, which will be a cause of skin damage.

Particularly in repeated administrations, a site of the skin (which will hereinafter be called "adhesion site"), on which attachment/release of an adhesive on an electrode pad is repeated, often have a lower electric resistance due to exfoliation of the stratum corneum. When a medicament reservoir comes into contact with the "adhesion site" because of gap of attached positions of the electrode pad during repeated administrations, highly concentrated medicament is inevitably absorbed into the skin, causing further skin damage.

Causes of such stimulation were analyzed in detail and a method of reducing the skin irritation was studied extensively. As a result, surprisingly, it has been found that the skin irritation due to electric current of the iontophoresis can be greatly reduced, only by preventing the contact between the "boundary surface" of an electrode pad and the human skin, without controlling the electric current by a complex apparatus/device such as electric resistors controlling the current. This means that the present invention makes it possible to prevent the "boundary surface", where electric current easily flows, from directly contacting with the human skin. As a result, the skin irritation due to the repeated administrations by the iontophoresis can be greatly reduced.

The iontophoresis electrode pad of the present invention comprises "a base sheet", "an electrode placed on the base sheet", "an adhesive sheet placed on the base sheet and having an opening, within which the electrode being exposed", and "a medicament reservoir containing a local anesthetic and placed in the opening of the adhesive sheet while being in contact with the electrode". The iontophoresis electrode pad is characterized in that: an inner peripheral surface of the opening of the adhesive sheet and an outer peripheral surface of the medicament reservoir are prevented from coming into contact with human skin while contacting with each other, and thereby skin irritation is reduced.

In a first specific aspect, the iontophoresis electrode pad has a boundary surface at which the inner peripheral surface of the opening of the adhesive sheet and the outer peripheral surface of the medicament reservoir contact with each other, and the boundary surface is covered with an insulating film.

In a second specific aspect, a predetermined space (r) is provided between the inner peripheral surface of the opening of the adhesive sheet and the outer peripheral surface of the medicament reservoir, and thickness of the adhesive sheet and thickness of the medicament reservoir are made substantially equal to each other.

In a third specific aspect, the medicament reservoir is dome shaped (gently curved shape lower than a hemisphere), which is higher than thickness of the adhesive sheet.

In this case, it is particularly preferred that at any points on surface of the medicament reservoir which come into contact with the human skin, sum of electric resistance of the medicament reservoir itself and contact electric resistance due to contact pressure with the human skin at that point is constant throughout an entire surface of the medicament reservoir.

Advantageous Effect of the Invention

With the iontophoresis electrode pad of the present invention having the above construction, the inner peripheral surface of the opening of the adhesive sheet and the outer peripheral surface of the medicament reservoir do not contact with each other with the human skin while contacting. Thanks to this, the above-mentioned <skin irritation 1> can be reduced.

Further, it is necessarily kept a region where the human skin do not contact therewith, between the "a site where the adhesive sheet contacts with the human skin" and "a site where the medicament reservoir contacts with the human skin". This region serves as a kind of margin, by which the above-mentioned <skin irritation 2> can be reduced.

Accordingly, the skin irritation can be reduced even when the iontophoresis electrode pad is repeatedly used.

BRIEF DESCRIPTION OF THE DRAWINGS

FIG. 5 shows an electrode pad of Referential Example 1.

FIG. 6 shows an electrode pad of Referential Example 2.

EMBODIMENTS FOR CARRYING OUT THE INVENTION

The iontophoresis electrode pad according to the present invention is characterized by that it is less skin irritating particularly, skin irritation caused by repeated administrations, regarding puncture pain relief. More specifically, as will be described in the following embodiments, the inner peripheral surface of the opening of the adhesive sheet and the outer peripheral surface of the medicament reservoir are prevented from coming into contact with each other with human skin while contacting, and thereby skin irritation is reduced.

Figure 1:
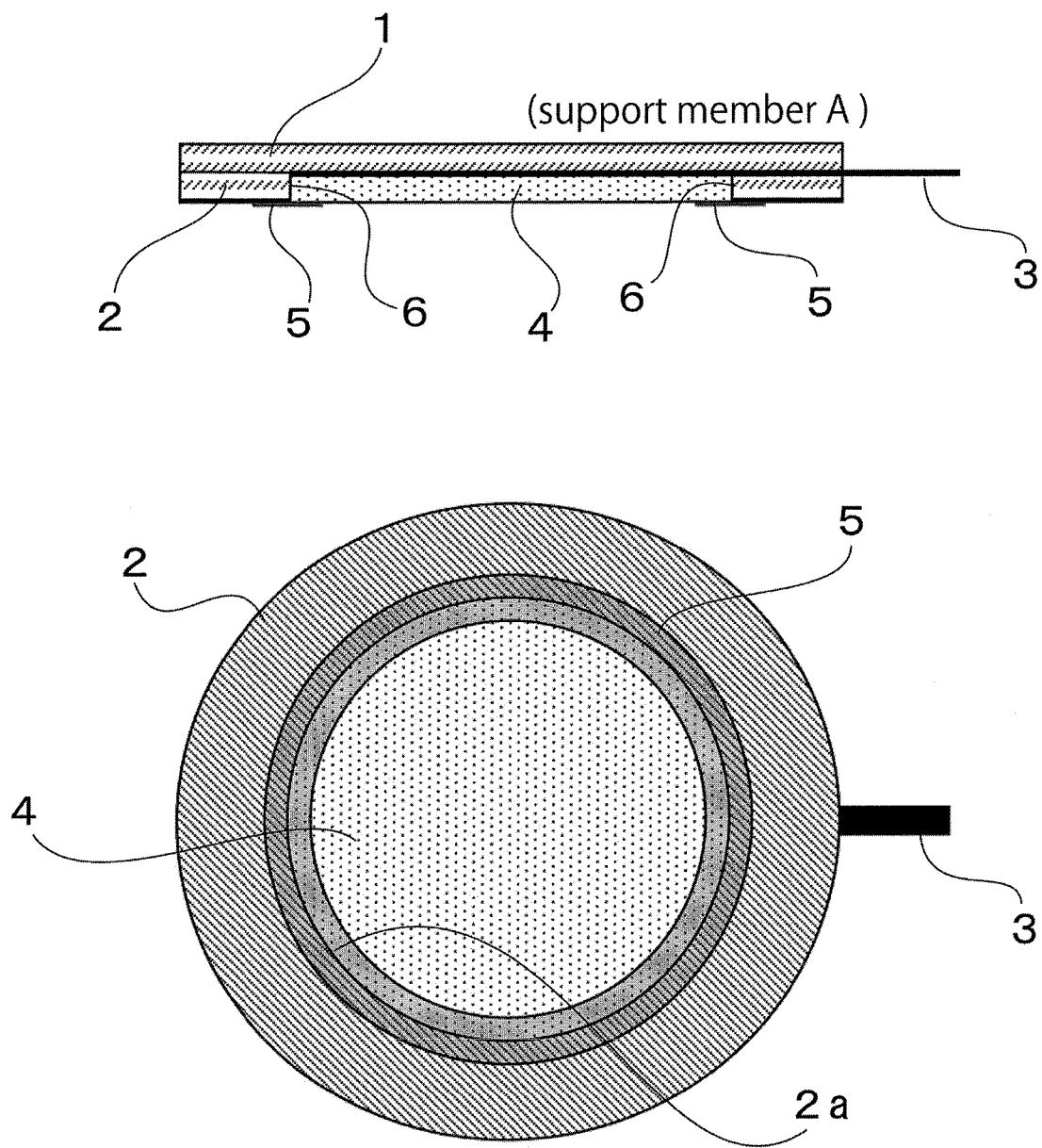
FIG. 1 shows an electrode pad according to a first embodiment of the present invention.

First Embodiment (FIG. 1)

As shown in FIG. 1, an electrode 3 is placed on a base sheet 1 (on the lower side of the sheet 1 in the drawing, and this is also true hereinafter). The electrode 3 protrudes outward to enable connection with an external apparatus, but on the base sheet, the electrode 3 extends within an area at least equal to that of a medicament reservoir 4.

Further thereon, an adhesive sheet 2 is placed. The adhesive sheet 2 has an adhesive layer on its surface, and this adhesive layer is to be fixed on human skin.

The adhesive sheet 2 has a circular opening 2a, and the electrode 3 is exposed in this opening 2a. Thereon, a medicament reservoir 4 is placed. The medicament reservoir 4 contains a local anesthetic, and is placed while being brought into contact with the electrode 3 in the opening 2a of the adhesive sheet.

In the first embodiment shown in FIG. 1, there exists a "boundary surface" 6 (boundary surface portion) at which the inner peripheral surface of the opening 2a of the adhesive sheet comes into contact with the outer peripheral surface of the medicament reservoir 4. This "boundary surface" 6 is covered with an insulating film 5.

Presence of this insulating film 5 prevents contact between the human skin and the "boundary surface", so that the skin irritation ([the skin irritation 1 described at the beginning] does not occur. Moreover, thanks to the insulating film provided between the medicament reservoir and the adhesive, an appropriate distance (margin) is kept between the adhesive and the medicament reservoir, so that the skin irritation [the skin irritation 2 described at the beginning] because of gap of attaching positions during repeated administrations hardly occurs.

Examples of a material of the insulating film 5 are polyvinyl chloride, polyvinylidene chloride, polypropylene, polyethylene, nylon, and urethane films. The insulating film 5 has preferably a width from 1 to 10 mm, more preferably from 2 to 5 mm.

An insulating film having a width less than 1 mm could not sufficiently cover the "boundary surface", and thus it may be impossible to prevent the stimulation. On the other hand, an insulating film having a width greater than 10 mm may substantially increases the pad size, and thus not preferable.

<Using Method>

When the electrode pad is practically used for the iontophoresis treatment, this pad is used together with another pad. The another pad is substantially the same to the pad shown in FIG. 1, except that "it does not contain a medicament in the medicament reservoir 4".

When these two pads are attached to human skin and an electric current is applied intradermally from the medicament reservoir 4 using an external apparatus, the local anesthetic is transdermally administered with the electric energy.

This using method is the same also in the second and the third embodiments, which will be described later.

Figure 2:
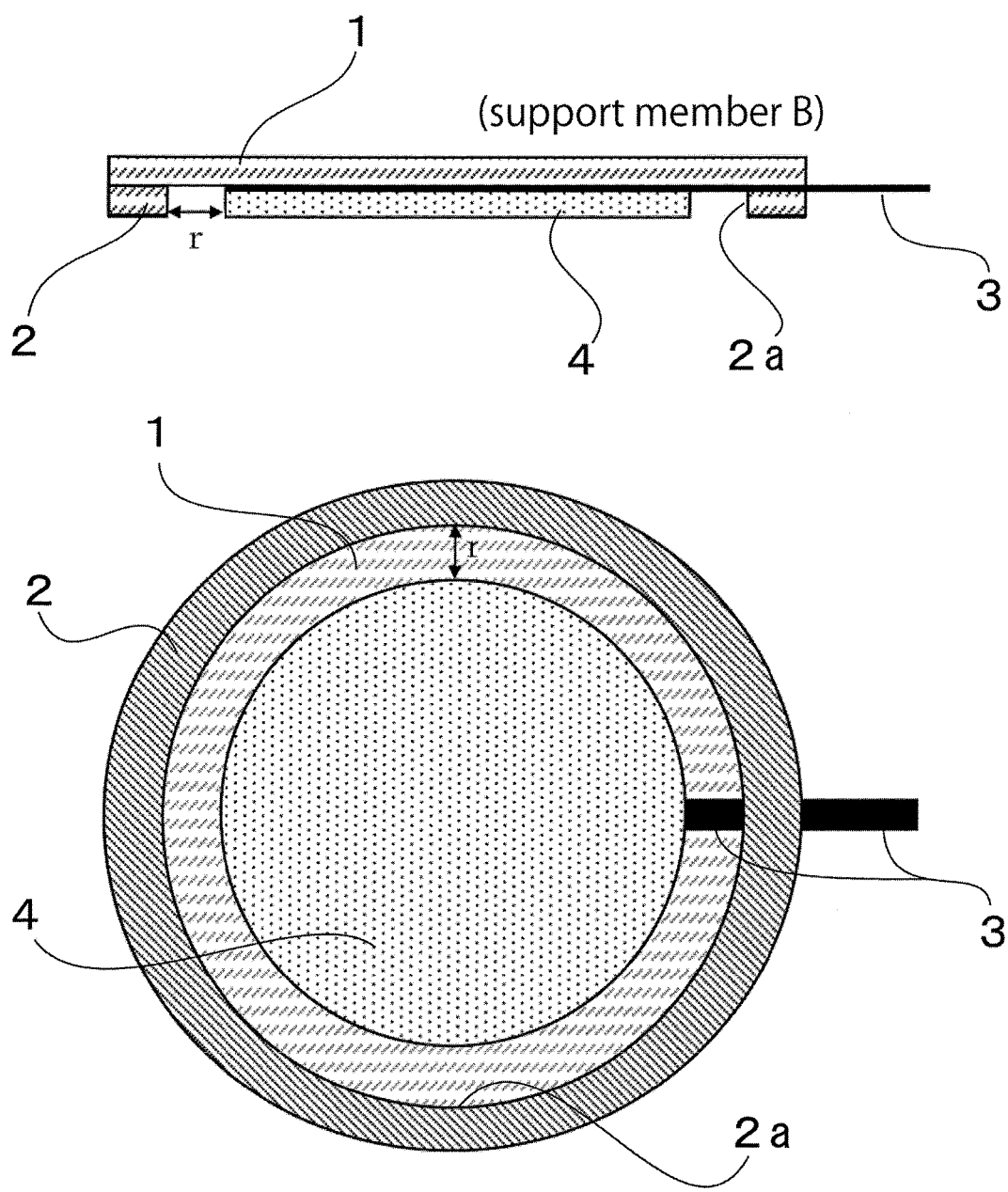
FIG. 2 shows an electrode pad according to a second embodiment of the present invention.

Second Embodiment (FIG. 2)

In the second embodiment, as shown in FIG. 2, a predetermined space (r) is provided between the inner peripheral surface of the opening 2a of the adhesive sheet 2 and the outer peripheral surface of the medicament reservoir 4. In the first embodiment, the "boundary surface" is covered with the insulating film 5, while in the second embodiment, the space (r) is provided so that the "boundary surface" itself does not exist.

Thus, in this embodiment, a site with a high current density ("boundary surface") does not exist so that the surface of the medicament reservoir is maintained at a constant current density, resulting in prevention of skin irritation [the skin irritation 1 described at the beginning].

Moreover, the space (r) serves as a margin, by which there hardly occurs the skin irritation [the skin irritation 2 described at the beginning] due to gap of the attaching positions of the electrode pad in repeated administrations.

The space (r) provided between the medicament reservoir 4 and the adhesive sheet 2 is preferably from about 1 to 10 mm, more preferably from 2 to 5 mm. When the space is less than 1 mm, the distance between the medicament reservoir 4 and the adhesive sheet 2 is too small, and thus there is a possibility of stimulation occurring due to gap of the attaching positions of the electrode pad in repeated administrations. On the other hand, the space more than 10 mm would substantially increase the size of the pad, and thus not preferable.

Note that, in the second embodiment, the height (thickness) of the adhesive sheet 2 and the medicament reservoir 4 with respect to the base sheet 1 are made almost equal with each other. As explained later, even if the space (r) is provided between the inner peripheral surface of the opening 2a of the adhesive sheet 2 and the outer peripheral surface of the medicament reservoir 4, an aimed advantageous effect cannot be attained when the height of the medicament reservoir 4 is too high, for example, when the medicament reservoir has just a hemispherical shape.

Figure 3:
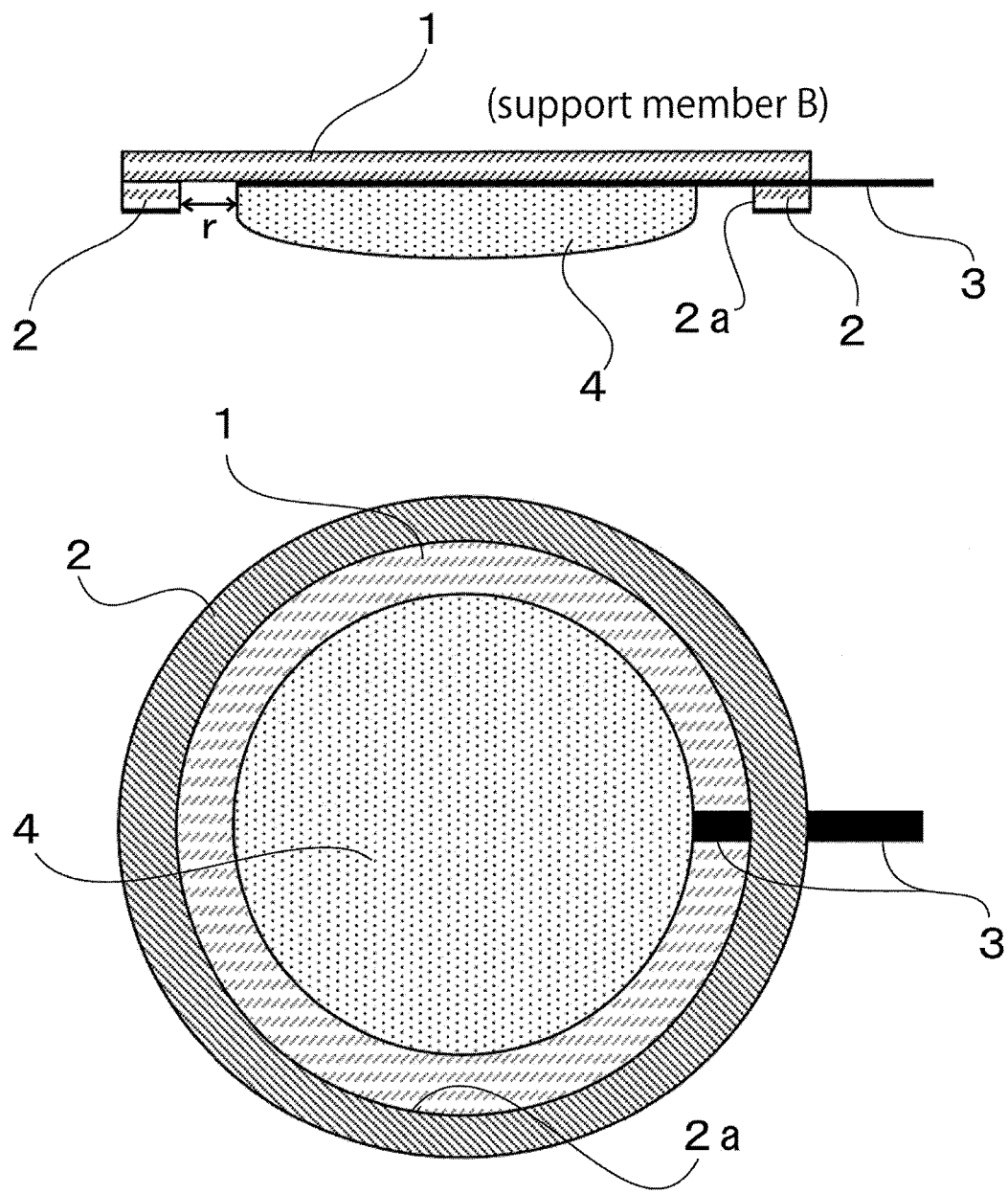
FIG. 3 shows an electrode pad according to a third embodiment of the present invention.

Third Embodiment (FIG. 3)

In the third embodiment, the height (thickness) of the medicament reservoir 4 with respect to the base sheet 1 is made greater than that of the adhesive sheet 2. When the electrode pad is attached to human skin, there appears a room around the reservoir 4 between the adhesive sheet 2 and the skin, because of the highness of the medicament reservoir 4. This room serves as a kind of a margin, which reduces the skin irritation [the skin irritation 2 described at the beginning].

Such the advantageous effect can also be attained even if the space (r) in FIG. 3 is not provided. That is, in FIG. 3, the outer peripheral surface of the medicament reservoir 4 can be in contact with the inner peripheral surface of the opening 2a.

When there is provided the space (r), a distance (the margin), kept between the site where the skin and the medicament reservoir 4 are in contact with and the site where the adhesive layer and the skin are in contact with, becomes larger. Thus, the effect for reducing the skin irritation [the skin irritation 2 described at the beginning] is enhanced.

But, when the height of the medicament reservoir 4 is made greater than that of the adhesive sheet 2 as in the third embodiment, the current density in the reservoir becomes uneven, depending on the shape of the medicament reservoir 4, which would sometimes cause skin irritation.

In order to prevent this skin irritation, the reservoir has preferably a shape in which, at any points on the reservoir surface which come into contact with the skin, the sum of the electric resistance of the medicament reservoir itself and the contact electric resistance due to the contact pressure with the skin at that point is constant throughout the entire surface of the reservoir. Examples of such the shape include gently curved shapes (dome and convex lens) as shown in FIG. 3.

On the other hand, Referential Examples 1 and 2 described next are undesirable examples.

Referential Example 1: FIG. 5

For example, if a medicament reservoir has a column-like shape, the contact pressure becomes non-uniform so that an excess current will flow at a corner of the column contacting with the skin. This could cause the skin irritation.

Referential Example 2: FIG. 6

If the height of a center portion of the medicament reservoir is made excessively greater than a member therearound, regardless that the medicament reservoir itself has low electric resistance, the contact pressure with the skin at the center portion of the medicament reservoir becomes abnormally higher than around of it. As a result, an excess current concentrates on the center portion, which would cause the skin irritation. This is not preferable.

Thus, it is not preferable that the shape of the medicament reservoir itself is made hemispheric, although a dome as shown in FIG. 3 is preferable.

In the case the medicament reservoir has a dome shape with a diameter of 5 to 40 mm, the height of the center portion is preferably 0.1 to 15 mm, and more preferably 0.5 to 5 mm. When the height difference is less than 0.1 mm, there is a possibility that the "boundary surface" comes into contact with the skin. On the other hand, when the height difference is more than 15 mm, there is a possibility that the contact pressure at the center portion becomes abnormally high, depending on the electric resistance in the medicament reservoir, which would cause the skin irritation. Thus, the height differences outside the above-mentioned range are not preferable.

Next, regarding the local anesthetic, the medicament reservoir, and the adhesive sheet, which are used in the electrode pad of the present invention, the materials of them and so will be described.

<Local Anesthetic>

In the present invention, any local anesthetic which is used generally can be employed, for example, lidocaine hydrochloride, dibucaine hydrochloride, tetracaine hydrochloride, oxybuprocaine hydrochloride, procaine hydrochloride, and bupivacaine hydrochloride. Among them, lidocaine hydrochloride is preferred.

In the present invention, the blending ratio of the local anesthetic is 0.3 to 2 wt %, more preferably 0.5 to 1.0 wt %. When the blending ratio of lidocaine is less than 0.3 wt %, sufficient local anesthetic effect cannot be given. On the other hand, even when the blending ratio exceeds 2.0 wt %, a dramatic effect cannot be expected, and besides, an amount of the medicament which would not work increases, resulting in disadvantage economically.

<Medicament Reservoir 4>

In the medicament reservoir 4 of the present invention, there is added a hydrophilic polymer, for example, agar, gelatin, agarose, xanthan gum, polyvinylpyrrolidone, locust bean gum, carrageenan, polyacrylic acid, pectin, glucomannan, polyacrylamide, and gellan gum. The blending ration of the hydrophilic polymer is 1 to 40%.

Further, in the medicament reservoir, if needed, there are added a preservative such as methylparaben and propylparaben, a humectant such as glycerin and propylene glycol, and purified water, and so.

<Adhesive Sheet 2>

The adhesive sheet 2 has an adhesive layer on its surface. The material of a base portion of the adhesive sheet 2 is, for example, polyethylene terephthalate, polyethylene, polypropylene, vinyl chloride resin, and laminated films or foamed materials thereof. In particular, a foamed polyurethane or polyethylene is preferred. A composite of them can also be used.

The adhesive sheet has an opening, of which the cross-sectional shape is circular, oblong, or rectangular.

For the adhesive layer on the surface, there is preferably used a hydrophobic adhesive, for example, rubber-based adhesive, acrylic adhesive, and silicon-based adhesive.

EXAMPLES

Examples of the present invention will next be described. It should however be noted that the scope of the present invention is not limited by the following examples. First, a "medicament gel solution" and a "saline gel solution" used in Examples will be described.

<Conductive Medicament-Containing Gel Solution (Hereinafter Referred to as "Medicament Gel Solution")>

0.5 g of lidocaine hydrochloride and 8 g of glycerin were dissolved in 74.5 g of purified water. In this solution, there was mixed a solution, which was obtained by dissolving 0.1 g of methylparaben and 0.05 g of propylparaben in 1.85 g of propylene glycol. Further, 15 g of polyvinyl alcohol is added and dissolved under heating, and thereafter, the resulting solution was cooled to room temperature.

<Physiological Saline Gel Solution (Hereinafter Referred to as "Saline Gel Solution")>

8 g of glycerin and 75 g of saline were mixed. In this mixture, there was mixed a solution, which was obtained by dissolving 0.1 g of methylparaben and 0.05 g of propylparaben in 1.85 g of propylene glycol. Further, 15 g of polyvinyl alcohol is added and dissolved under heating, and thereafter, the resulting solution was cooled to room temperature.

Example 1: FIG. 1

The (support member A) in FIG. 1 is comprised of a base sheet 1, a silver foil 3 (0.05 mm thick) as an electrode placed thereon, and a foam tape 2 (adhesive sheet: product of 3M, thickness: about 1 mm) placed thereon. The foam tape 2 is cut out at the center portion to have a circle, from which the silver foil is exposed. The foam tape has, on the surface thereof, an adhesive layer.

Into this circle of the (support member A), the "medicament gel solution" is poured, and then, freezing and thawing were done to form an electrode pad. Further, the boundary surface between the foam tape and the "medicament gel solution" is covered with a ring-shaped urethane film (insulating film 5) to complete the electrode pad, which is shown in FIG. 1.

Example 2: FIG. 2

The (support member B) in FIG. 2 is different from the (support member A) of Example 1 in that a ring-shaped foam member is inserted inside of the circle.

The "medicament gel solution" was poured inside this ring-shaped foam member, and then, freezing and thawing were done to form an electrode pad. Then, the ring-shaped foam member is removed gently to complete the electrode pad, which is shown in FIG. 2.

Example 3: FIG. 3

A support member the same as the (support member B) of Example 2 was used. A watch glass filled with the "medicament gel solution" therein was attached to the center circle of this support member, and then, freezing and thawing were done to form an electrode pad. Then, the watch glass and the ring-shaped foam member were removed to complete the electrode pad, which is shown in FIG. 3.

Figure 4:
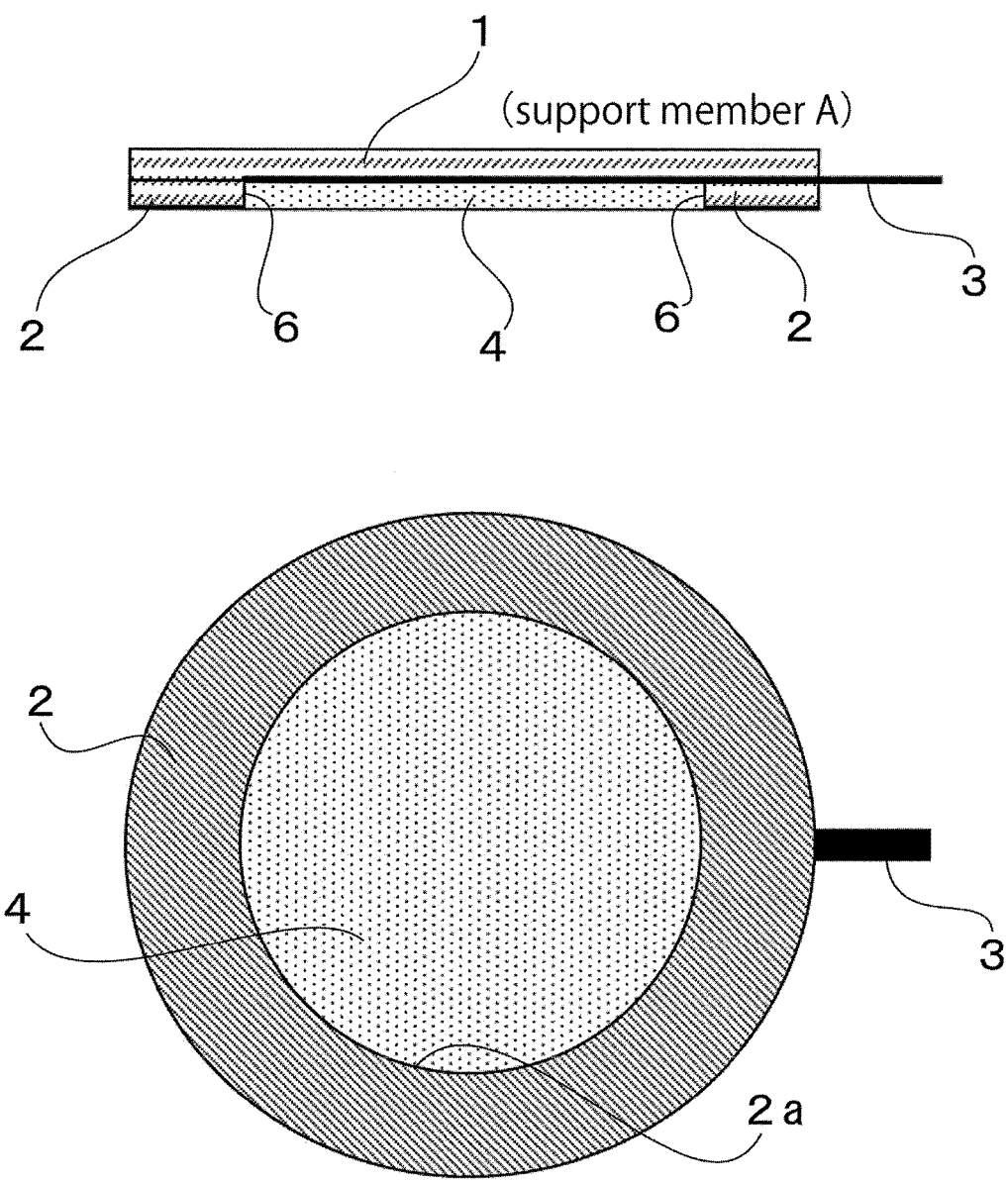
FIG. 4 shows an electrode pad of Comparative Example.
Figure 7:
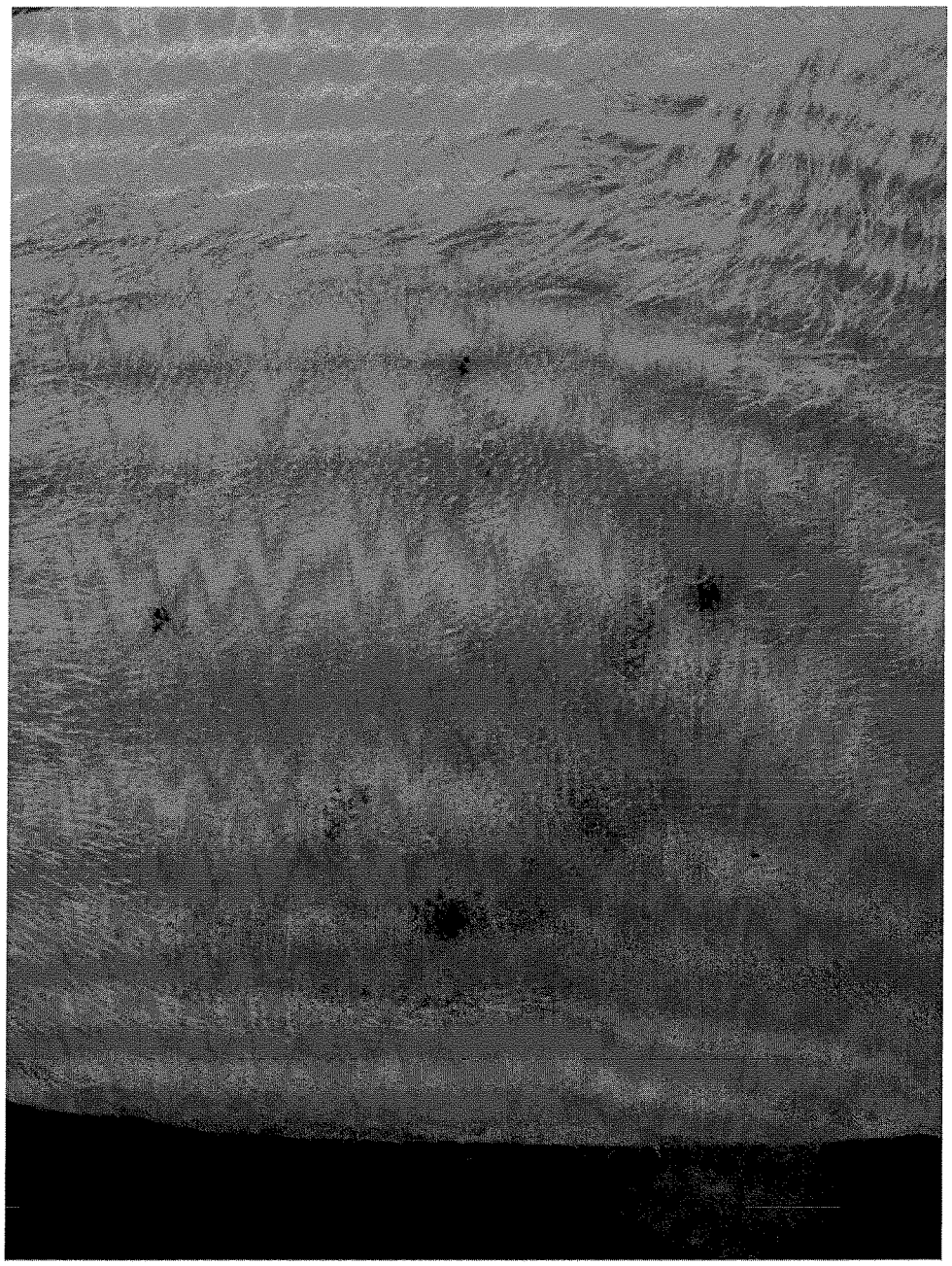
FIG. 7 is Photograph 1 showing the skin condition when the electrode pad of Example 1 was applied repeatedly to back of a rat, in Test 1.
Figure 8:
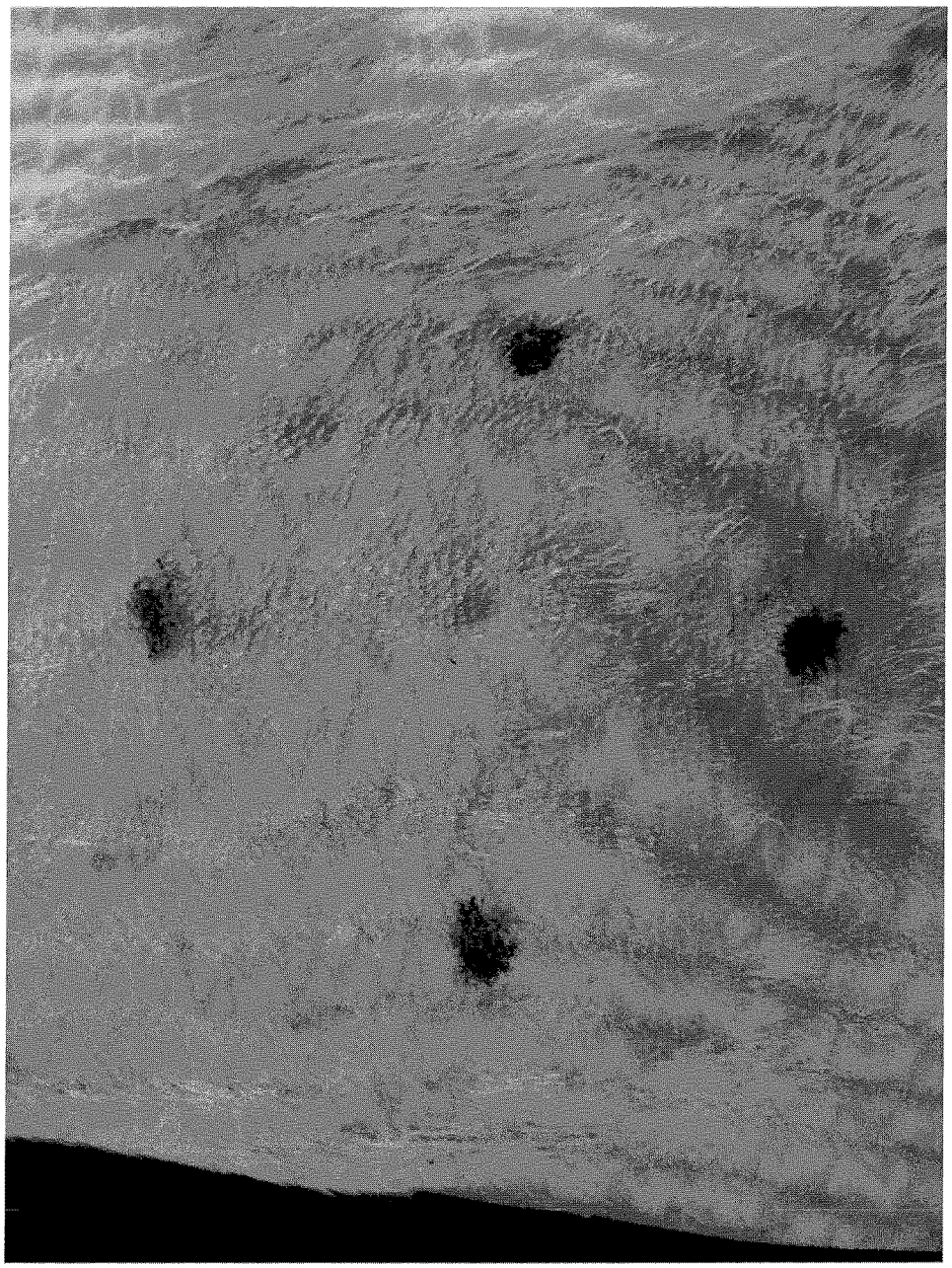
FIG. 8 is Photograph 2 showing the skin condition when the electrode pad of Example 2 was applied repeatedly to back of a rat, in Test 1.
Figure 9:
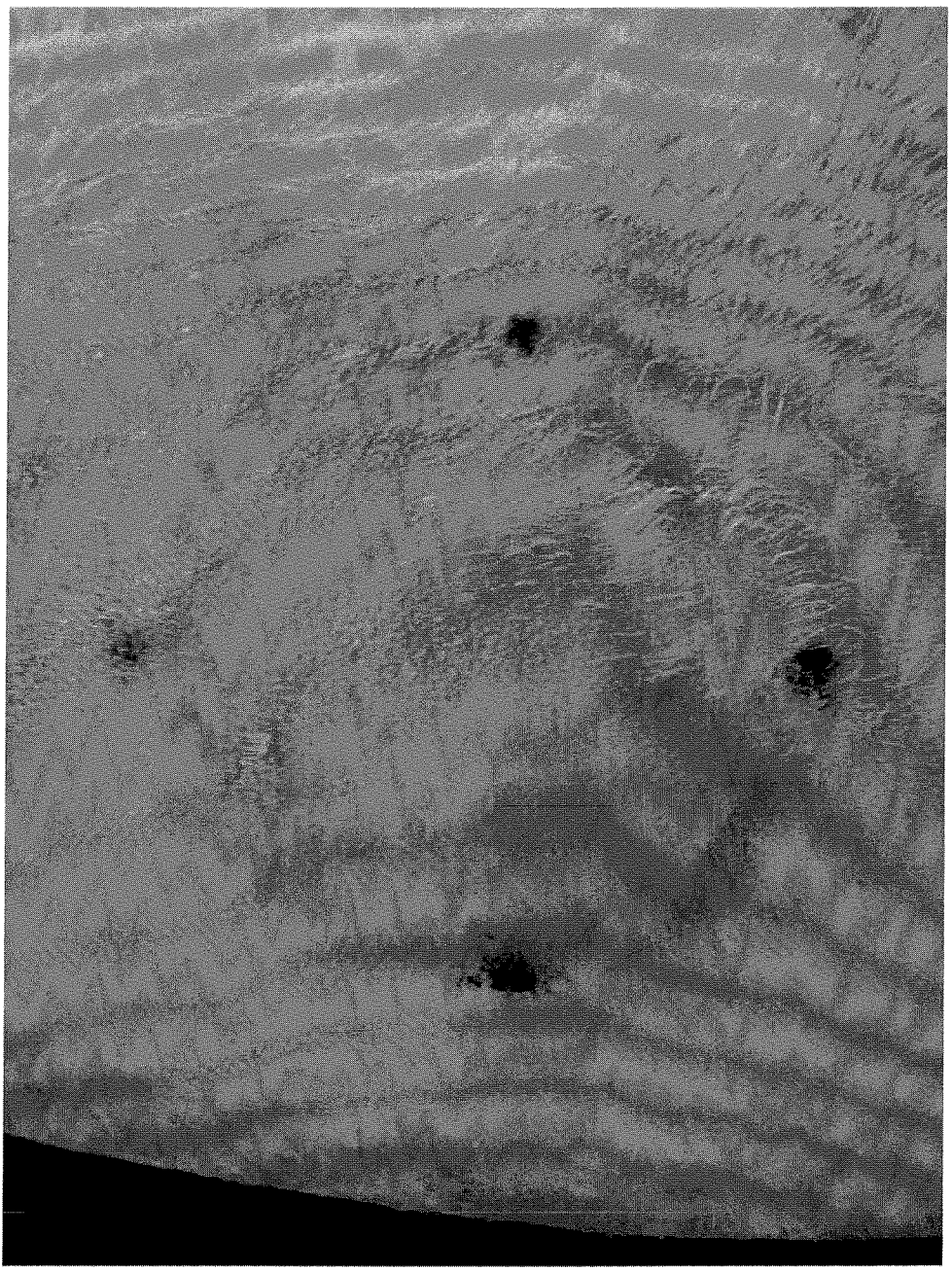
FIG. 9 is Photograph 3 showing the skin condition when the electrode pad of Comparative Example was applied repeatedly to back of a rat, in Test 1.
Figure 10:
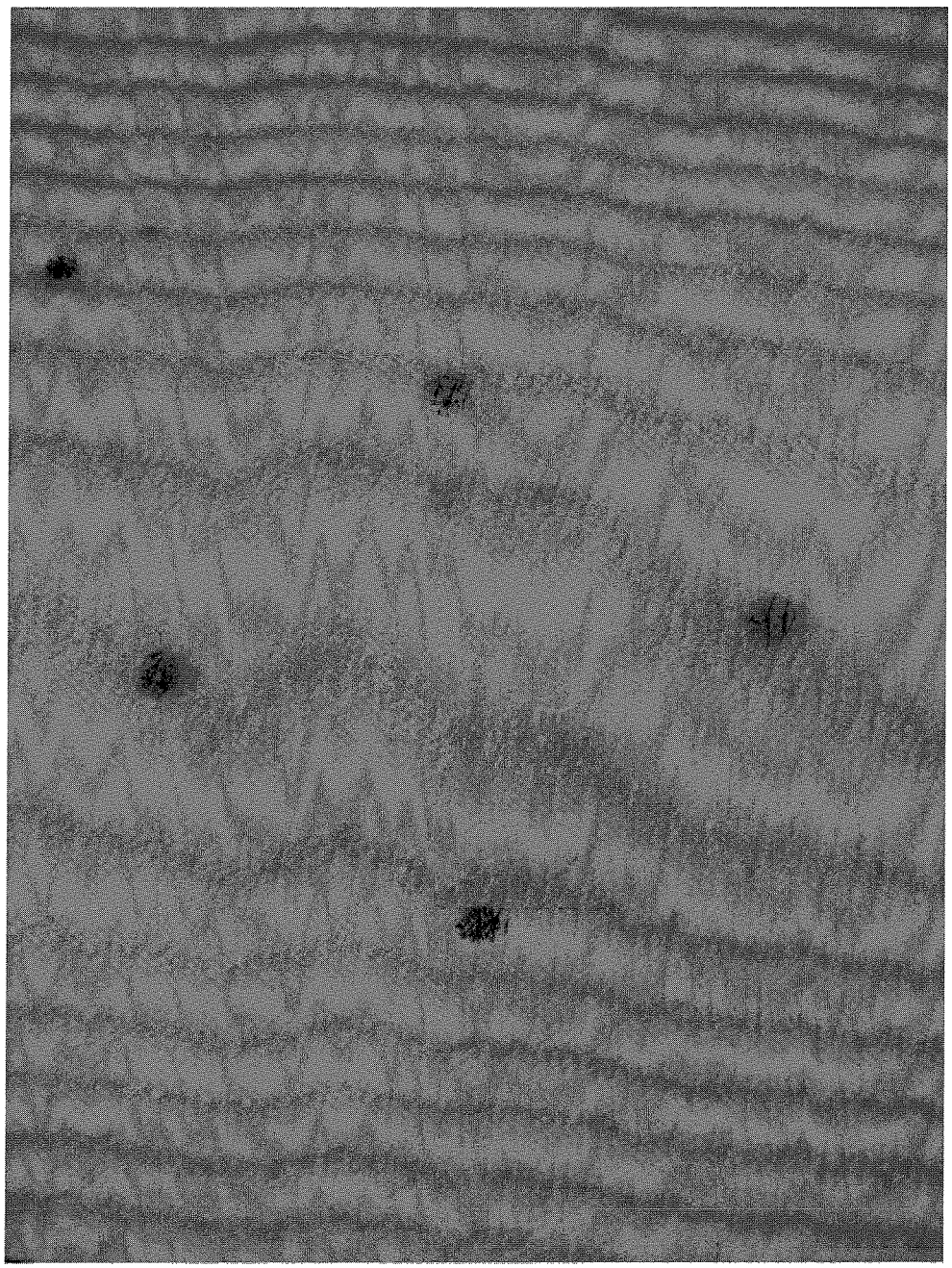
FIG. 10 is Photograph 4 showing the skin condition when the electrode pad of Example 2 was applied repeatedly to the forearm of a volunteer, in Test 2.
Figure 11:
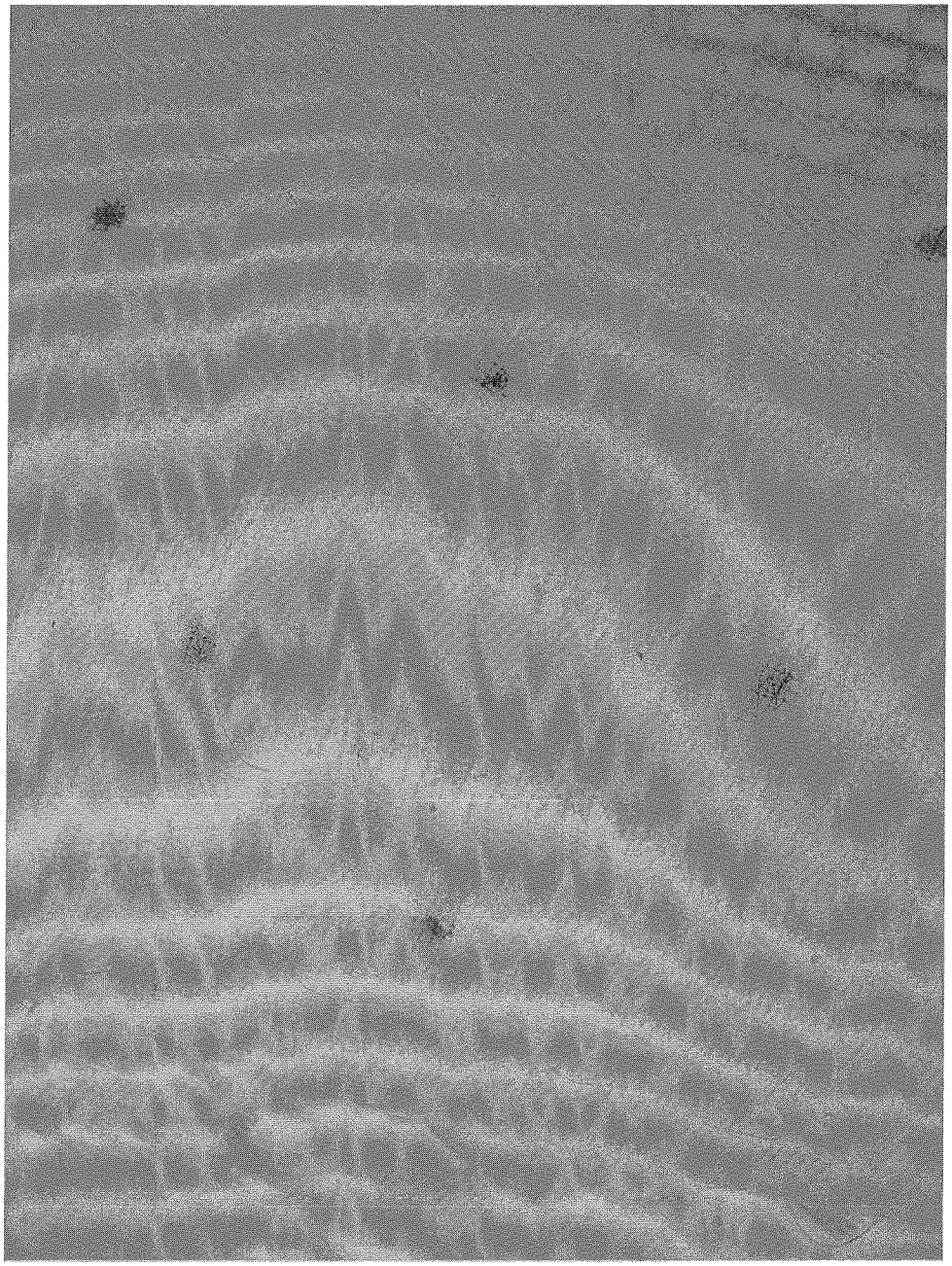
FIG. 11 is Photograph 5 showing the skin condition when the electrode pad of Example 3 was applied repeatedly to the forearm of a volunteer, in Test 2.
Figure 12:
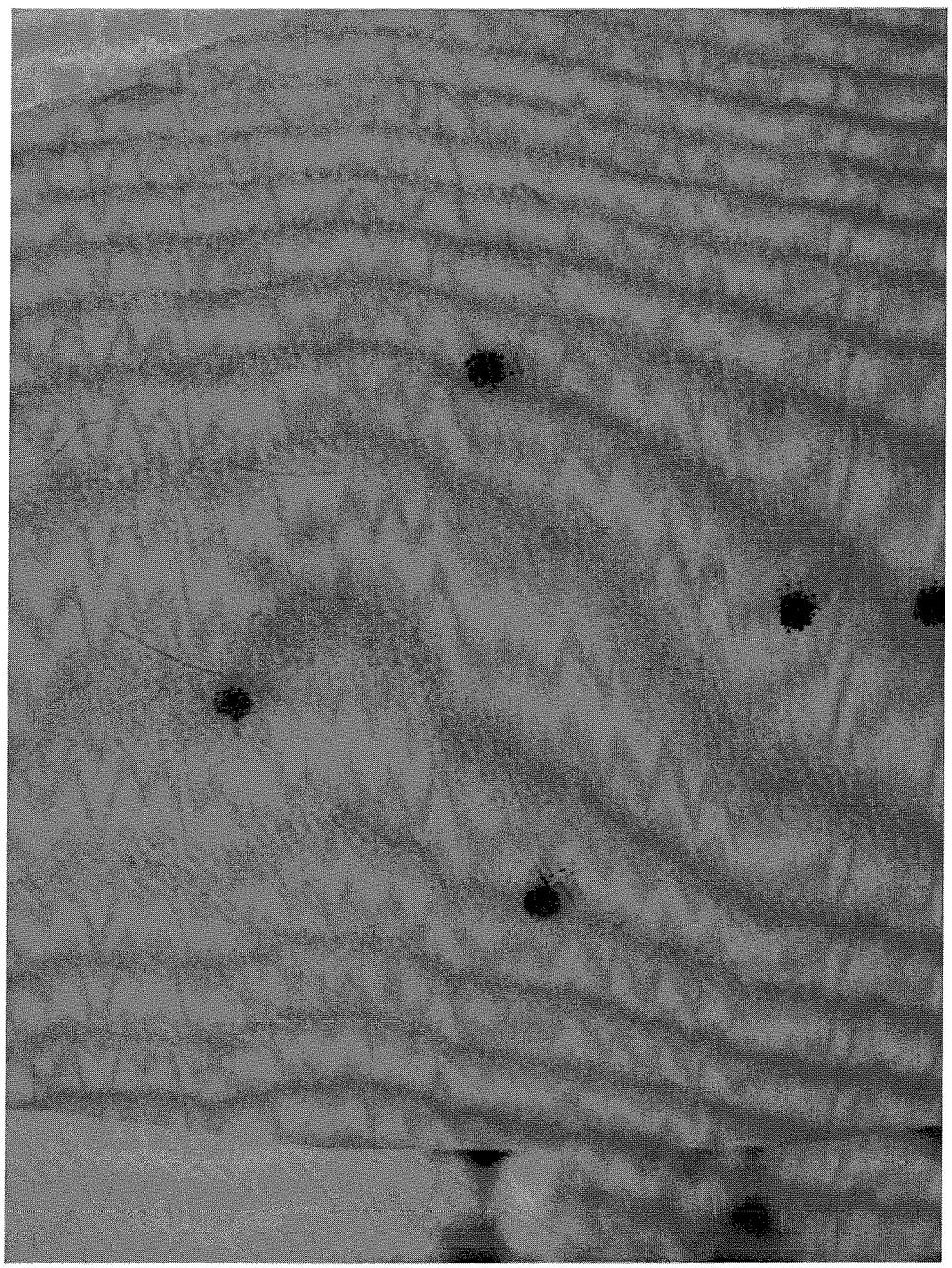
FIG. 12 is Photograph 6 showing the skin condition when the electrode pad of Comparative Example was applied repeatedly to the forearm of a volunteer, in Test 2.
Figure 13:
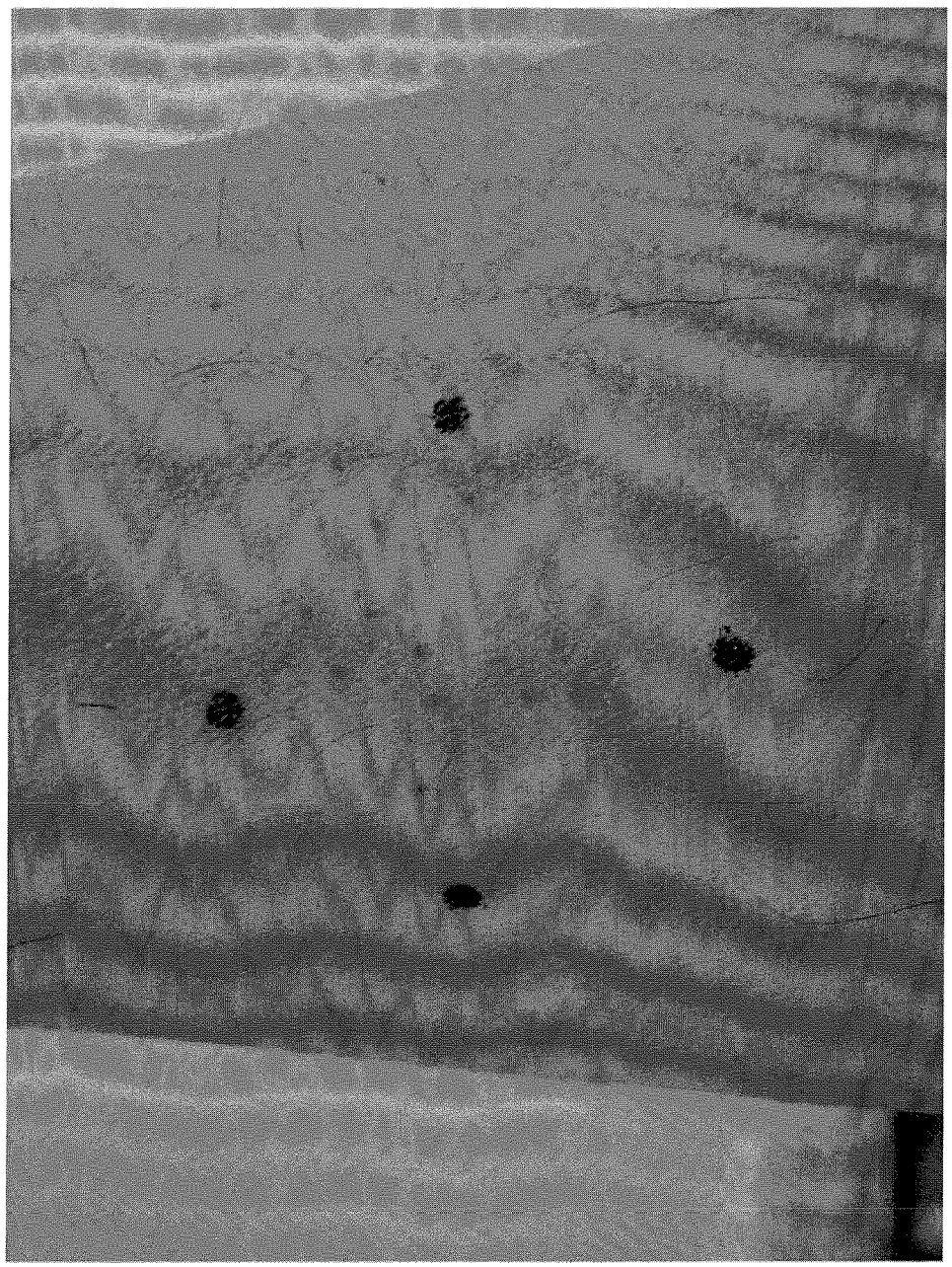
FIG. 13 is Photograph 7 showing the skin condition when the electrode pad of Referential Example 2 was applied repeatedly to the forearm of a volunteer, in Test 2.

Comparative Example: FIG. 4

The "medicament gel solution" was poured in a support member the same as the (support member A) of Example 1, and then, freezing and thawing were done to complete the electrode pad, which is shown in FIG. 4.

Referential Example 1: FIG. 5

On a support member the same as the (support member A) of Example 1, a foam member (with release agent) was laminated, which has an opening aligned with the center circle of the support member. The "medicament gel solution" was poured in the opening, and then, freezing and thawing were done to form an electrode pad. From this electrode pad, the foam member (with releasing agent) was gently removed to complete the electrode pad, which is shown in FIG. 5.

Referential Example 2: FIG. 6

The electrode pad shown in FIG. 6 was obtained in a similar manner in Example 3, except that a hemispherical chill tray was used instead of the watch glass.

The following tests were conducted, using the electrode pads obtained as above.

<Test 1>

Figure 14:
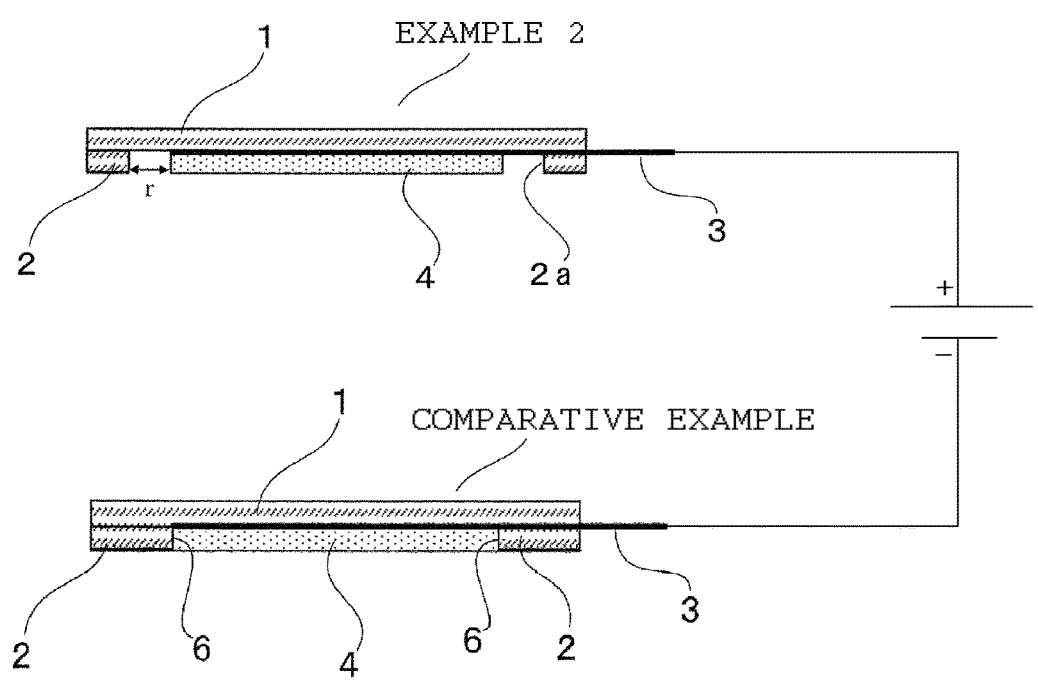
FIG. 14 shows an example of Test 1 and Test 2 in which the electrode pad of Example 2 is connected to an anode of a DC power supply and the electrode pad of the Comparative Example is connected to a cathode of the DC power supply.

Using the electrode pads of Examples 1, 2, and Comparative Example, administrations were repeated to rats, and the skin irritation was studied. The "saline gel solution" was poured in the (support member A) as in the comparative example, and then, freezing and thawing were done to form a saline gel electrode pad (hereinafter, referred to as saline patch). The saline patch was attached to a hair shaved back of rats. An anode of a DC power supply was connected to the pad and a cathode was connected to the saline patch, and electric current of 0.3 mA/cm$^2$ for 10 minutes was applied. FIG. 14 shows an example of Test 1 in which the electrode pad of Example 2 is connected to the anode of the DC power supply and the electrode pad of the Comparative Example, as the saline patch, is connected to the cathode of the DC power supply. This operation was conducted once a day for 5 days, and the skin reaction at the administered site was observed. The results are shown in Table 1.

As a result, regarding the Comparative Example, after 3 or 4 times of administrations, burn-like stimulation occurred around the gel. After 5 times of administrations, accumulation of heavy burn-like stimulation was observed (Photograph 3), which did not disappear for a few days after administrations. Stimulation was observed also regarding Examples 1 and 2, but it was lighter (Photographs 1 and 2) than that observed in the Comparative Example.

TABLE 1

Skin irritation caused by repeated administrations to rats

| | Kind of stimulation | Stimulation appeared at: | Intensity of stimulation * | Referred to: |
|---|---|---|---|---|
| Example 1 | Burn-like stimulation | Periphery of medicament reservoir (partial) | ++ | Photograph 1 |
| Example 2 | Erythema | Discrete | ± | Photograph 2 |
| Comp. Ex. | Burn-like stimulation | Periphery of medicament reservoir (entire edge) | +++ | Photograph 3 |

* Intensity of stimulation:
±: weak stimulation
+: slightly strong stimulation
++: strong stimulation
+++: considerably strong stimulation <Test 2>

Using the electrode pads of Examples 2, 3, Comparative Example, and Referential Example 2, administrations were repeated to inside of forearm of human volunteers, and the skin irritation was studied. The pad and the saline patch were attached to the inside of the forearm of the volunteers. An anode of a DC power supply was connected to the pad and a cathode is connected to the saline patch, and electric current of 0.2 mA/cm$^2$ for 10 minutes was applied. FIG. 14 shows an example of Test 2 in which the electrode pad of Example 2 is connected to the anode of the DC power supply and the electrode pad of the Comparative Example, as the saline patch, is connected to the cathode of the DC power supply. This operation was conducted every other day totally 9 times (regarding the Comparative Example and Referential Example, the operation was conducted 5 times). After the final administration, the skin reaction at the administered site was observed. The results are shown in Table 2.

Regarding the Comparative Example and the Referential Example, in spite of less frequency of current application than that in each of the Examples, strong burn-like stimulation occurred, in the Comparative Example at around the gel, and in the Referential Example at the center of the gel (Photographs 6 and 7). On the other hand, regarding the Example 2, erythema appeared (Photograph 4), but it was light enough to disappear after a few days. Regarding the Example 3, also erythema appeared (Photograph 5), but it was light enough to disappear on the next day.

TABLE 2

Skin irritation caused by repeated administrations to volunteers

| | Kind of stimulation | Stimulation appeared at: | Intensity of stimulation * | Referred to: |
|---|---|---|---|---|
| Example 2 | Erythema | Entire surface of medicament reservoir | + | Photograph 4 |
| Example 3 | Erythema | Entire surface of medicament reservoir | ± | Photograph 5 |
| Comp. Ex. | Burn-like stimulation | Periphery of medicament reservoir (entire edge) | ++ | Photograph 6 |
| Ref. Ex. 2 | Burn-like stimulation | Discrete at the center of medicament reservoir | ++ | Photograph 7 |

* Intensity of stimulation:
±: weak stimulation
+: slightly strong stimulation
++: strong stimulation
+++: considerably strong stimulation It has been confirmed from the above results that the iontophoresis electrode pad according to the present invention has considerably high safety even when it is used for repeated administrations.

INDUSTRIAL APPLICABILITY

For alleviating a puncture pain, the present invention can provide an iontophoresis formulation (electrode pad) capable of safely administering a local anesthetic. The electrode pad of the present invention can be used for alleviating a puncture pain, also for blood dialysis wherein the puncture is conducted every day or every other day.

DESCRIPTION OF REFERENCE NUMERALS

1. Base sheet
2. Adhesive sheet (foam tape)
3. Electrode (silver foil)
4. Medicament reservoir
5. Non-tacky insulating film
6. Boundary surface

The invention claimed is:

1. An electrode pad used for iontophoresis treatment comprising:
a base sheet;
an electrode placed on the base sheet;
an adhesive sheet placed on the base sheet and having an opening, within which the electrode being exposed;
a medicament reservoir containing a local anesthetic and placed in the opening of the adhesive sheet such that a first surface of the medicament reservoir is in direct contact with the electrode, and such that a second surface of the medicament reservoir is arranged to be in direct contact with human skin, the first and second surfaces being opposite surfaces of the medicament reservoir; and
an insulating film, wherein:
the electrode pad has a boundary surface portion at which an inner peripheral surface of the opening of the adhesive sheet and an outer peripheral surface of the medicament reservoir directly contact each other, and the boundary surface portion is covered with the insulating film such that a first surface of the insulating film is in direct contact with the adhesive sheet and the medicament reservoir, and such that a second surface of the insulating film is arranged to be in direct contact with human skin, the first and second surfaces of the insulating film being opposite surfaces; and
the boundary surface portion is prevented from coming into contact with human skin by the insulating film, and thereby skin irritation is reduced.

2. The electrode pad according to claim 1, wherein the opening of the adhesive sheet is circular and the insulating film is ring-shaped with a width of 1 to 10 mm.

3. An electrode pad used for iontophoresis treatment in which the electrode pad is connected to an anode of a power supply and another pad which does not include medicament is connected to a cathode of the power supply, the electrode pad comprising: a base sheet; an electrode placed on the base sheet; an adhesive sheet placed on the base sheet and having an opening, within which the electrode being exposed, the electrode pad being adhered to human skin using only the adhesive sheet; and a medicament reservoir containing a local anesthetic and placed in the opening of the adhesive sheet such that a first surface of the medicament reservoir is in direct contact with the electrode, and such that a second surface of the medicament reservoir is arranged to be in direct contact with human skin, the first and second surfaces being opposite surfaces of the medicament reservoir, wherein: a predetermined space (r) is provided between an inner peripheral surface of the opening of the adhesive sheet and an outer peripheral surface of the medicament reservoir, the space (r) being an empty space, such that the inner peripheral surface of the opening of the adhesive sheet and the outer peripheral surface of the medicament reservoir are prevented from coming into contact with each other while contacting human skin, and thereby skin irritation is reduced; and a thickness of the adhesive sheet and a thickness of the medicament reservoir are made substantially equal to each other.

4. The electrode pad according to claim 3, wherein the space (r) is 1 to 10 mm.

5. An electrode pad used for iontophoresis treatment in which the electrode pad is connected to an anode of a power supply and another pad which does not include medicament is connected to a cathode of the power supply, the electrode pad comprising: a base sheet; an electrode placed on the base sheet; an adhesive sheet placed on the base sheet and having an opening, within which the electrode being exposed, the electrode pad being adhered to human skin using only the adhesive sheet; and a medicament reservoir containing a local anesthetic and placed in the opening of the adhesive sheet such that a first surface of the medicament reservoir is in direct contact with the electrode, and such that a second surface of the medicament reservoir is arranged to be in direct contact with human skin, the first and second surfaces being opposite surfaces of the medicament reservoir, wherein: a predetermined space (r) is provided between an inner peripheral surface of the opening of the adhesive sheet and an outer peripheral surface of the medicament reservoir, the space (r) being an empty space, such that the inner peripheral surface of the opening of the adhesive sheet and the outer peripheral surface of the medicament reservoir are prevented from coming into contact with each other while contacting human skin, and thereby skin irritation is reduced; and the medicament reservoir is dome shaped, and a height of the dome shaped medicament reservoir is greater than a thickness of the adhesive sheet.

6. The electrode pad according to claim 5, wherein at any point on a surface of the medicament reservoir which comes into contact with the human skin, a sum of electric resistance of the medicament reservoir itself and contact electric resistance due to contact pressure with the human skin at that point is constant throughout an entire surface of the medicament reservoir.

* * * * *